(12) United States Patent
Kubik

(10) Patent No.: US 8,785,731 B2
(45) Date of Patent: *Jul. 22, 2014

(54) CANOLA PLANTS WITH HIGH OLEIC AND LOW LINOLENIC

(75) Inventor: Thomas J. Kubik, Saskatoon (CA)

(73) Assignee: Dow AgroSciences, LLC., Indianapolis, IN (US)

( * ) Notice: Subject to any disclaimer, the term of this patent is extended or adjusted under 35 U.S.C. 154(b) by 1169 days.

This patent is subject to a terminal disclaimer.

(21) Appl. No.: 12/060,726

(22) Filed: Apr. 1, 2008

(65) Prior Publication Data

US 2009/0093367 A1   Apr. 9, 2009

Related U.S. Application Data

(63) Continuation-in-part of application No. 11/238,263, filed on Sep. 29, 2005, now Pat. No. 7,355,100, which is a continuation-in-part of application No. 11/238,407, filed on Sep. 29, 2005, now Pat. No. 7,348,473, which is a continuation-in-part of application No. 11/397,150, filed on Apr. 4, 2006, now Pat. No. 7,456,340, which is a continuation-in-part of application No. 11/397,106, filed on Apr. 4, 2006, now abandoned.

(60) Provisional application No. 60/614,886, filed on Sep. 30, 2004, provisional application No. 60/614,888, filed on Sep. 30, 2004, provisional application No. 60/667,576, filed on Apr. 4, 2005, provisional application No. 60/668,204, filed on Apr. 4, 2005.

(51) Int. Cl.
*A01H 5/00* (2006.01)
*A01H 5/10* (2006.01)
*A01H 1/00* (2006.01)
*C12N 15/82* (2006.01)

(52) U.S. Cl.
USPC .......................... 800/306; 800/260; 435/430

(58) Field of Classification Search
None
See application file for complete search history.

(56) References Cited

U.S. PATENT DOCUMENTS

| 5,523,520 | A | | 6/1996 | Hunsperger et al. | |
|---|---|---|---|---|---|
| 5,770,789 | A | * | 6/1998 | Mitchell-Olds et al. | 800/265 |
| 6,444,879 | B1 | | 9/2002 | Sernyk | |
| 6,720,481 | B1 | * | 4/2004 | Patel et al. | 800/306 |
| 7,335,817 | B2 | | 2/2008 | Patel | |
| 7,348,473 | B2 | * | 3/2008 | Kubik | 800/306 |
| 7,355,100 | B2 | * | 4/2008 | Kubik | 800/306 |
| 7,456,340 | B2 | * | 11/2008 | Kubik | 800/306 |
| 7,595,177 | B2 | * | 9/2009 | Barnes et al. | 435/91.2 |
| 2002/0138881 | A1 | | 9/2002 | Charne et al. | |

FOREIGN PATENT DOCUMENTS

EP          0 242 246          10/1987
WO      WO 2007/053482       5/2007

OTHER PUBLICATIONS

Aslam et al, Plant Breeding 128 (4): 348-355, 2009.*
Yaniv et al, Industrial Crops and Products 3: 247-251, 1995.*
Bennetzen et al., "Approaches and progress in the molecular cloning of plant disease resistance genes," In Genetic Engineering, 1992, pp. 99-124, vol. 14, J.K. Stetlow, Plenum Press, NY.
Cheung, et al., Conservation of S-locus for self incompatibility in *Brassica napus* (L) and *Brassica oleracea* (L). Theor, Appl. Genet., 1997, pp. 73-82, vol. 95.
Eshed et al., "Less-than-additive epistatic interactions of quantitative trait loci in tomato." Genetics, 1996, pp. 1807-1817, vol. 143.
Kott et al., "The role of biotechnology in canola/rapeseed research." In Rapeseed Production, Chemistry, Nutrition, and Processing Technology, 1990, pp. 47-78, Van Reinhold, NY.
Kraft et al., "Linkage disequilibrium and fingerprinting in sugar beet." Theor. App. Genet., 2000, pp. 323-326, vol. 101.
Poehlman, J. M., et al., "Sleper, Methods in Plant Breeding, in Breeding Field Crops," 4th ed. (1995) Iowa State University Press, Ames, Iowa, p. 173.
Economic Analysis, Canola Pricing System, accessed Oct. 5, 2011, 6 pages.
Top crop manager, Weed control courtesy of plant breeders, http://www.topcropmanager.com/content/view/1942/67, accessed Oct. 5, 2011, 2 pages.
Earle, et al., 1994, Cold-tolerant Ogura CMS *Brassica* vegetables for horticultural use. Cruciferase Newsletter 16:80-81.
Pang et al., 1992, Expression of a gene encoding a scorpion insectotoxin peptide in yeast, bacteria and plants. Gene, 1992, 116:165-172.

* cited by examiner

*Primary Examiner* — Elizabeth McElwain
(74) *Attorney, Agent, or Firm* — Marcia I. Rosenfeld; Kenneth B. Ludwig; TraskBritt, P.C.

(57) ABSTRACT

Canola plants with high oleic acid and low linolenic acid content are disclosed. In addition, the canola plants of the invention are resistant to imidazolinone herbicides and are resistant to blackleg. The canola plants of the invention also have low total glucosinolate content. There is also provided a method for controlling weeds in a field of canola plants wherein the canola plants are herbicide resistant.

24 Claims, No Drawings

CANOLA PLANTS WITH HIGH OLEIC AND LOW LINOLENIC

BACKGROUND OF THE INVENTION

This application is a continuation-in-part of the following applications: U.S. application Ser. No. 11/238,263, filed Sep. 29, 2005 1) U.S. Pat. No. 7,355,100, issued Apr. 8, 2008, which claims the benefit of U.S. Provisional Application No. 60/614,886, filed Sep. 30, 2004; 2) U.S. application Ser. No. 12/060,726, filed Apr. 1, 2008 U.S. Pat. No. 7,348,473 issued Mar. 25, 2008, which claims the benefit of U.S. Provisional Application No. 60/614,888, filed Sep. 30, 2004; 3) U.S. application Ser. No. 11/397,150, filed Apr. 4, 2006, issued as U.S. Pat. No. 7,456,340, which claims the benefit of U.S. Provisional Application No. 60/667,576, filed Apr. 4, 2005; and 4) U.S. application Ser. No. 11/397,106, filed Apr. 4, 2006, now abandoned, which claims the benefit of U.S. Provisional Application No. 60/668,204, filed Apr. 4, 2005, all of which are hereby incorporated by reference in their entirety.

The present invention relates to canola plants having imidazolinone resistance, high oleic acid content, low linolenic acid content and blackleg resistance. All publications cited in this application are herein incorporated by reference.

Canola produces an oil that has the lowest saturated fat content of any vegetable oil. Today, there is an increasing demand for this oil by diet-conscious consumers.

Canola is a genetic variation of rapeseed developed by Canadian plant breeders specifically for its nutritional qualities, particularly its low level of saturated fat. In 1956 the nutritional aspects of rapeseed oil were questioned, especially concerning the high eicosenoic and erucic fatty acid contents. In the early 1960's, Canadian plant breeders isolated rapeseed plants with low eicosenoic and erucic acid contents. The Health and Welfare Department recommended conversion to the production of low erucic acid varieties of rapeseed. Industry responded with a voluntary agreement to limit erucic acid content to five percent in food products, effective Dec. 1, 1973.

In 1985, the U.S. Food and Drug Administration recognized rapeseed and canola as two different species based on their content and uses. Rapeseed oil is used in industry, while canola oil is used for human consumption. High erucic acid rapeseed (HEAR) oil contains 22-60 percent erucic acid, while low erucic acid rapeseed (LEAR) oil has less than 2 percent erucic acid. Meal with less than 30 µmol/g glucosinolates is from canola. Livestock can safely eat canola meal, but high glucosinolate rapeseed meal should only be fed to cattle because it may cause thyroid problems in monogastric livestock.

Each canola plant produces yellow flowers that, in turn, produce pods similar in shape to pea pods but about ⅕th the size. Within the pods are tiny round seeds that are crushed to obtain canola oil. Each seed contains approximately 40 percent oil. The remainder of the seed is processed into canola meal, which is used as a high protein livestock feed.

Because it is perceived as a "healthy" oil, its use has risen steadily both as a cooking oil and in processed foods. The consumption of canola oil is expected to surpass corn and cottonseed oils, becoming second only to soybean oil. It is low in saturates, high in monounsaturates, and contains a high level of oleic acid. Many people prefer the light color and mild taste of canola oil over olive oil, the other readily available oil high in monounsaturates.

Rapeseed has been grown in India for more than 3000 years and in Europe since the 13th century. The 1950s saw the start of large scale rapeseed production in Europe. Total world rapeseed/canola production is more than 22.5 million metric tons.

Farmers in Canada began producing canola oil in 1968. Early canola cultivars were known as single zero cultivars because their oil contained 5 percent or less erucic acid, but glucosinolates were high. In 1974, the first licensed double zero cultivars (low erucic acid and low glucosinolates) were grown. Today all canola cultivars are double zero cultivars. Canola has come to mean all rapeseed cultivars that produce oil with less than 2 percent erucic acid and meal with less than 30 µmol/g of glucosinolates.

Canola production uses small grain equipment, limiting the need for large investments in machinery. Planting costs of canola are similar to those for winter wheat. The low investment costs and increasing consumer demand for canola oil make it a good alternative crop.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior canola cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same canola traits.

Each year, the plant breeder selects the germplasm to advance to the next generation. This germplasm is grown under unique and different geographical, climatic and soil conditions and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new canola cultivars.

The development of new canola cultivars requires the development and selection of canola varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max* L. Merr.) p 6.131-6.138 in S. J. O'Brien (ed) *Genetic Maps: Locus Maps of Complex Genomes*, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus with as many as 26 alleles. (Diwan, N. and Cregan, P. B., *Theor. Appl. Genet.* 95:22-225, 1997.) SNPs may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162, 967. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into canola varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., *Theor. Appl. Genet.*, 77:889-892, 1989.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Canola, *Brassica napus* oleifera annua, is an important and valuable field crop. Thus, a continuing goal of plant breeders is to develop stable, high yielding canola cultivars that are agronomically sound. To accomplish this goal, the canola breeder must select and develop canola plants that have traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

According to the invention, there is provided a canola seed comprising imidazolinone resistance and oleic acid content of greater than 70%. The canola seed further comprises less than 3% linolenic acid. In another aspect a canola plant produced from said seed further comprises blackleg (*Leptosphaeria maculans*) resistance.

In another aspect, there is provided a canola seed comprising imidazolinone resistance and oleic acid content between 70.1% and 72.0%.

In another aspect, there is provided a canola seed comprising imidazolinone resistance and oleic acid content between 72.1% and 74.0%.

In another aspect, there is provided a canola seed comprising imidazolinone resistance and oleic acid content between 74.1% and 76.0%.

In another aspect, there is provided a canola seed comprising imidazolinone resistance and oleic acid content greater than 70.0% and further comprising linolenic acid content less than 3.0%.

In another aspect, there is provided a canola seed comprising imidazolinone resistance and oleic acid content greater than 70.0% and further comprising linolenic acid content between 2.0% and 2.99%.

In another aspect, there is provided a canola seed comprising imidazolinone resistance and oleic acid content greater than 70.0% and further comprising linolenic acid content between 1.0% and 1.99.

In another aspect, there is provided a canola seed comprising imidazolinone resistance and oleic acid content greater than 70.0% and further comprising linolenic acid content between 0.5% and 0.99%.

In another aspect, there is provided a canola seed comprising imidazolinone resistance and oleic acid content greater than 70.0% and less than 3.0% linolenic acid content and a canola plant produced from said seed further comprising blackleg (*Leptosphaeria maculans*) resistance.

In another aspect, the present invention comprises a canola hybrid seed comprising imidazolinone resistance and oleic acid content of greater than 70%. In another aspect the canola hybrid seed further comprises less than 3% linolenic acid. In another aspect there is provided a canola plant produced from said seed further comprising blackleg (*Leptosphaeria maculans*) resistance.

In another aspect, the present invention comprises a canola hybrid seed comprising imidazolinone resistance and oleic acid content between 70.1% and 72.0%.

In another aspect, the present invention comprises a canola hybrid seed comprising imidazolinone resistance and oleic acid content between 72.1% and 74.0%.

In another aspect, the present invention comprises a canola hybrid seed comprising imidazolinone resistance and oleic acid content between 74.1% and 76.0%.

In another aspect, there is provided a canola hybrid seed comprising imidazolinone resistance and oleic acid content greater than 70.0% and further comprising linolenic acid content less than 3.0%.

In another aspect, there is provided a canola hybrid seed comprising imidazolinone resistance and oleic acid content greater than 70.0% and further comprising linolenic acid content between 2.0% and 2.99%.

In another aspect, there is provided a canola hybrid seed comprising imidazolinone resistance and oleic acid content greater than 70.0% and further comprising linolenic acid content between 1.0% and 1.99%.

In another aspect, there is provided a canola hybrid seed comprising imidazolinone resistance and oleic acid content greater than 70.0% and further comprising linolenic acid content between 0.5% and 0.99%.

In another aspect, there is provided a canola hybrid seed comprising imidazolinone resistance and oleic acid content greater than 70.0% and less than 3.0% linolenic acid content and a canola plant produced from said seed further comprising blackleg tolerance or resistance.

In another aspect, there is provided a canola seed comprising imidazolinone resistance and oleic acid content greater than 70.0% and total glucosinolate content of less than 12.0 μm/g of seed.

In another aspect, there is provided a canola seed comprising imidazolinone resistance and oleic acid content greater than 70.0% and total glucosinolate content between 10.0 μm/g and 11.99 μm/g of seed.

In another aspect, there is provided a canola seed comprising imidazolinone resistance and oleic acid content greater than 70.0% and total glucosinolate content between 8.0 μm/g and 9.99 μm/g of seed.

In another aspect, there is provided a canola seed comprising imidazolinone resistance and oleic acid content greater than 70.0% and total glucosinolate content between 7.0 μm/g and 7.99 μm/g of seed.

In another aspect, there is provided a canola hybrid seed comprising imidazolinone resistance and oleic acid content greater than 70.0% and total glucosinolate content of less than 12.0 μm/g of seed In another aspect, there is provided a canola hybrid seed comprising imidazolinone resistance and oleic acid content greater than 70.0% and total glucosinolate content between 10.0 μm/g and 11.99 μm/g of seed.

In another aspect, there is provided a canola hybrid seed comprising imidazolinone resistance and oleic acid content greater than 70.0% and total glucosinolate content between 8.0 μm/g and 9.99 μm/g of seed.

In another aspect, there is provided a canola hybrid seed comprising imidazolinone resistance and oleic acid content greater than 70.0% and total glucosinolate content between 7.0 μm/g and 7.99 μm/g of seed.

In another aspect, there is provided a method for controlling at least one weed in a field, wherein said field contains at least one high oleic imi resistant canola plant, wherein said method comprises applying to at least a portion of said field an imi herbicide.

In a further aspect, there is provided a method for controlling at least one weed in a field, wherein said field contains at least one high oleic, imi resistant and glyphosate resistant canola plant, wherein said method comprises applying to at least a portion of said field an imi herbicide and a glyphosate herbicide.

In a further aspect, there is provided a method for controlling at least one weed in a field, wherein said field contains at least one high oleic, imi resistant, glyphosate resistant, and glufosinate resistant canola plant, wherein said method comprises applying to at least a portion of said field an imi herbicide, a glyphosate herbicide, and a glufosinate herbicide.

In a further aspect, there is provided a method for controlling at least one weed in a field, wherein said field contains at least one high oleic, imi resistant, glyphosate resistant, glufosinate resistant, and 2, 4-D resistant canola plant, wherein said method comprises applying to at least a portion of said field an imi herbicide, a glyphosate herbicide, a glufosinate herbicide, and a 2, 4-D herbicide.

In addition to the exemplary aspects and embodiments described above, further aspects and embodiments will become apparent by reference to the drawings and by study of the following descriptions.

DEFINITIONS

In the description and tables which follow, a number of terms are used. In order to provide a clear and consistent understanding of the specification and claims, including the scope to be given such terms, the following definitions are provided:

2, 4-D herbicide. As used herein, 2, 4-D is an herbicide that consists of auxin, a plant growth regulator. 2, 4-D is a member of the phenoxy family of herbicides. Some examples of 2, 4-D herbicides include, but are not limited to, PAR II, Trillion, Tri-Kil, Killex Aqua-Kleen, Barrage, Lawn-Keep, Malerbane, Planotox, Plantgard, Savage, Salvo, Weedone, and Weedtrine-II and Weedaway.

2, 4-D resistance. As used herein, 2, 4-D resistance also includes resistance to auxins and tolerance to 2, 4-D herbicides and auxins. 2, 4-D resistance is conferred by one or more genes, alleles or events which block the action of 2, 4-D allowing a plant to survive application of a 2, 4-D herbicide.

Allele. Allele is any of one or more alternative forms of a gene, all of which relate to one trait or characteristic. In a diploid cell or organism, the two alleles of a given gene occupy corresponding loci on a pair of homologous chromosomes.

Anther arrangement. The orientation of the anthers in fully opened flowers can also be useful as an identifying trait. This can range from introse (facing inward toward pistil), erect (neither inward not outward), or extrose (facing outward away from pistil).

Anther dotting. The presence/absence of anther dotting (colored spots on the tips of anthers) and if present, the percentage of anther dotting on the tips of anthers in newly opened flowers is also a distinguishing trait for varieties.

Anther fertility. Anther fertility is a measure of the amount of pollen produced on the anthers of a flower. It can range from sterile (such as in female parents used for hybrid seed production) to fertile (all anthers shedding).

Backcrossing. Backcrossing is a process in which a breeder repeatedly crosses hybrid progeny back to one of the parents, for example, a first generation hybrid $F_1$ with one of the parental genotypes of the $F_1$ hybrid.

Blackleg resistance/tolerance. Resistance or tolerance to blackleg (*Leptosphaeria maculans*) is measured on a scale of 1-5 where 1 is the most resistant and 5 is the least resistant. Resistant canola plants have a resistance score that ranges from 0.85 to 1.32, moderately resistant canola plants' score ranges from 1.36 to 2.0, moderately susceptible canola plants' score ranges from 2.15 to 2.3, and susceptible canola plants' score ranges from 2.9 to 5.0.

Check average. Average for one or more checks in a given location.

Cotyledon width. The cotyledons are leaf structures that form in the developing seeds of canola which make up the majority of the mature seed of these species. When the seed germinates, the cotyledons are pushed out of the soil by the growing hypocotyls (segment of the seedling stem below the cotyledons and above the root) and they unfold as the first photosynthetic leafs of the plant. The width of the cotyledons varies by variety and can be classified as narrow, medium, or wide.

Disease resistance. As used herein, the term "disease resistance" is defined as the ability of plants to restrict the activities of a specified pest, such as an insect, fungus, virus, or bacterial.

Disease tolerance. As used herein, the term "disease tolerance" is defined as the ability of plants to endure a specified pest (such as an insect, fungus, virus or bacteria) or an adverse environmental condition and still perform and produce in spite of this disorder.

Elite canola cultivar. A canola cultivar, per se, which has been sold commercially.

Elite canola parent cultivar. A canola cultivar which is the parent cultivar of a canola hybrid that has been commercially sold.

Embryo. The embryo is the small plant contained within a mature seed.

FAME analysis. Fatty Acid Methyl Ester analysis is a method that allows for accurate quantification of the fatty acids that make up complex lipid classes.

Flower bud location. The location of the unopened flower buds relative to the adjacent opened flowers is useful in distinguishing between the canola species. The unopened buds are held above the most recently opened flowers in *B. napus* and they are positioned below the most recently opened flower buds in *B. rapa*.

Flowering date. Flowering date is measured by the number of days from planting to the stage when 50% of the plants in a population have one or more open flowers. This varies from variety to variety.

Glufosinate herbicide. As used herein, a glufosinate herbicide is an herbicide that interferes with the biosynthetic pathway of the amino acid glutamine and with ammonia detoxification. Examples of glufosinate herbicides include, but are not limited to, BASTA, RELY, FINALE, CHALLENGE and LIBERTY.

Glufosinate resistance. As used herein, glufosinate resistance also includes tolerance to glufosinate herbicides. Glufosinate resistance is conferred by one or more genes, alleles or events which block the action of glufosinate allowing a plant to survive application of a glufosinate herbicide.

Glyphosate herbicide. As used herein, a glyphosate herbicide is an herbicide that interferes with the enzyme 5-enolpyruvylshikimate-3-phosphate synthase in a plant which eventually results in the death of the plant. An example of a glyphosate herbicide is ROUNDUP.

Glyphosate resistance. As used herein, glyphosate resistance also includes tolerance to glyphosate herbicides. Glyphosate resistance is conferred by one or more genes, alleles or events which alter the enzyme 5-enolpyruvylshikimate-3-phosphate synthase allowing the enzyme to resist or tolerate the action of glyphosate herbicides.

Growth habit. At the end of flowering, the angle relative to the ground surface of the outermost fully expanded leaf petioles is a variety specific trait. This trait can range from erect (very upright along the stem) to prostrate (almost horizontal and parallel with the ground surface).

High oleic. As used herein, high oleic means canola seeds having an oleic acid content of greater than 70.0%.

Imidazolinone (imi) herbicide. As used herein, an imidazolinone (imi) herbicide is an herbicide that interferes with the action of the enzyme acetolactate synthase (ALS), also known as acetohydroxy acid synthase (AHAS), in a plant which eventually results in the death of the plant. Examples of imi herbicides include, but are not limited to, imazamethbenz, imazamox, imazapic, imazapyr, imazaquin, and imazethapyr.

Imidazolinone resistance (imi). As used herein, imi resistance also includes tolerance to imi herbicides. Imi resistance is conferred by one or more genes, alleles or events which alter acetolactate synthase (ALS), also known as acetohydroxy acid synthase (AHAS) allowing the enzyme to resist or tolerate the action of imidazolinone herbicides.

Leaf attachment to the stem. The leaf attachment to the stem trait is especially useful for distinguishing between the two canola species. The base of the leaf blade of the upper stem leaves of *B. rapa* completely clasp the stem whereas those of the *B. napus* only partially clasp the stem. Those of the mustard species do not clasp the stem at all.

Leaf blade color. The color of the leaf blades is variety specific and can range from light to medium dark green to blue green.

Leaf development of lobes. The leaves on the upper portion of the stem can show varying degrees of development of lobes which are disconnected from one another along the petiole of the leaf. The degree of lobing is variety specific and can range from absent (no lobes)/weak through very strong (abundant lobes).

Leaf glaucosity. Leaf glaucosity refers to the waxiness of the leaves and is characteristic of specific varieties although environment can have some effect on the degree of waxiness. This trait can range from absent (no waxiness)/weak through very strong. The degree of waxiness can be best determined by rubbing the leaf surface and noting the degree of wax present.

Leaf indentation of margin. The leaves on the upper portion of the stem can also show varying degrees of serration along the leaf margins. The degree of serration or indentation of the leaf margins can vary from absent (smooth margin)/weak to strong (heavy saw-tooth like margin).

Leaf pubescence. The leaf pubescence is the degree of hairiness of the leaf surface and is especially useful for distinguishing between the canola species. There are two main classes of pubescence which are glabrous (smooth/not hairy) and pubescent (hairy) which mainly differentiate between the *B. napus* and *B. rapa* species, respectively.

Leaf surface. The leaf surface can also be used to distinguish between varieties. The surface can be smooth or rugose (lumpy) with varying degrees between the two extremes.

Maturity. The maturity of a variety is measured as the number of days between planting and physiological maturity. This is useful trait in distinguishing varieties relative to one another.

Mean Yield. Mean yield of all canola entries grown at a given location.

Oil content. Oil content is measured as percent of the whole dried seed and is characteristic of different varieties. It can be determined using various analytical techniques such as NMR, NIR, FAME analysis and Soxhlet extraction.

Oil percent D.B. Oil content expressed as a weight percent corrected for moisture.

Percent linolenic acid. Percent linolenic acid is the percent oil of the seed that is linolenic acid as determined by FAME analysis.

Percent oleic acid (OLE). Percent oleic acid is the percent oil of the seed that is oleic acid as determined by FAME analysis.

Percentage of total fatty acids. The percentage of total fatty acids is determined by extracting a sample of oil from seed, producing the methyl esters of fatty acids present in that oil sample and analyzing the proportions of the various fatty acids in the sample using gas chromatography. The fatty acid composition can be a distinguishing characteristic of a variety.

Petal color. The petal color on the first day a flower opens can be a distinguishing characteristic for a variety. It can be white, varying shades of yellow or orange.

Plant. As used herein, the term "plant" includes plant cells, plant protoplasts, plant cell tissue cultures from which canola plants can be regenerated and plant cells that are intact in plants or parts of plants, such as embryos, pollen, ovules, flowers, leaves, roots, root tips, anthers, cotyledons, hypocotyls, stems, pistils, and the like.

Plant height. Plant height is the height of the plant at the end of flowering if the floral branches are extended upright (i.e., not lodged). This varies from variety to variety and although it can be influenced by environment, relative comparisons between varieties grown side by side are useful for variety identification.

Protein content. Protein content is measured as percent of whole dried seed and is characteristic of different varieties. This can be determined using various analytical techniques such as NIR and Kjeldahl.

Resistance to lodging. Resistance to lodging measures the ability of a variety to stand up in the field under high yield conditions and severe environmental factors. A variety can have good (remain upright), fair, or poor (falls over) resistance to lodging. The degree of resistance to lodging is not expressed under all conditions but is most meaningful when there is some degree of lodging in a field trial. Lodging is rated on a scale of 1 to 5 where 1 is erect and 5 is flat on the ground.

Seed coat color. The color of the seed coat can be variety specific and can range from black through brown through yellow. Color can also be mixed for some varieties.

Seed coat mucilage. Seed coat mucilage is useful for differentiating between the two species of canola with *B. rapa* varieties having mucilage present in their seed coats whereas *B. napus* varieties do not have this present. It is detected by imbibing seeds with water and monitoring the mucilage that is exuded by the seed.

Seedling growth habit. The rosette consists of the first 2-8 true leaves and a variety can be characterized as having a strong rosette (closely packed leaves) or a weak rosette (loosely arranged leaves).

Silique (pod) habit. Silique habit is a trait which is variety specific and is a measure of the orientation of the pods along the racemes (flowering stems). This trait can range from erect (pods angled close to racemes) through horizontal (pods perpendicular to racemes) through arching (pods show distinct arching habit).

Silique (pod) length of beak. The beak is the segment at the end of the pod which does not contain seed (it is a remnant of the stigma and style for the flower). The length of the beak can be variety specific and can range form short through medium through long.

Silique (pod) length of pedicel. The pedicel is the stem that attaches the pod to the raceme of flowering shoot. The length of the pedicel can be variety specific and can vary from short through medium through long.

Silique (Pod) length. Silique length is the length of the fully developed pods and can range from short to medium to long. It is best used by making comparisons relative to reference varieties.

Silique (pod) type. The silique type is typically a bilateral single pod for both species of canola and is not really useful for variety identification within these species.

Silique (pod) width. Silique width is the width of the fully developed pods and can range from narrow to medium to wide. It is best used by making comparisons relative to reference varieties.

Single gene converted (conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stem intensity of anthocyanin coloration. The stems and other organs of canola plants can have varying degrees of purple coloration which is due to the presence of anthocyanin (purple) pigments. The degree of coloration is somewhat subject to growing conditions, but varieties typically show varying degrees of coloration ranging from: absent (no purple)/very weak to very strong (deep purple coloration).

Total glucosinolates. Total glucosinolates are measured in micromoles ($\mu$m) and includes all glucosinolates (all forms not just aliphatic glucosinolates) per gram of air-dried oil-free meal. The level of glucosinolates is somewhat influenced by the sulfur fertility of the soil, but is also controlled by the genetic makeup of each variety and thus can be useful in characterizing varieties.

Total saturated (TOTSAT). Total percent oil of the seed of the saturated fats in the oil including C12:0, C14:0, C16:0, C18:0, C20:0, C22:0 and C24:0.

Transgenic/transgene. A transgenic canola plant possesses one or more genes, alleles or events that have been transferred into canola from a different species. A transgene is a gene, allele or event that is transferred between species. The transfer of a transgene can occur through plant breeding techniques or through recombinant DNA techniques well known in the art.

Yield. Greater than 10% above the mean yield across 10 or more locations.

DETAILED DESCRIPTION OF THE INVENTION

The present invention provides for canola seeds having high oleic acid content, low linolenic acid content and canola plant with blackleg resistance. Oleic acid is an omega-9 fatty acid which is often referred to as being a "heart healthy" fat. Studies have shown that oleic acid can lower cholesterol, homocysteine and C-reactive protein in humans (Carrero, J. J. et al. (2007). Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program. *J. Nutr.* 137:384-390; Natali, F. et al. (2007). Oleic acid is a potent inhibitor of fatty acid and cholesterol synthesis in C6 glioma cells. *J. Lipid Res.* 48:1966-1975). There is some indication that oleic acid may inhibit certain types of cancer cells (Menendez, J. A. et al. (2005). Oleic acid, the main monounsaturated fatty acid of olive oil, suppresses Her-2/neu (erbB-2) expression and synergistically enhances the growth inhibitory effects of trastuzumab (Herceptin™) in breast cancer cells with Her-2/neu oncogene amplification. *Ann. Oncology*. Published online Jan. 10, 2005). The present invention provides canola seeds with high oleic acid content, including oleic acid seed content of between 70.1% and 72.0%. In another aspect, there is provided a canola seed comprising imidazolinone resistance and oleic acid content between 72.1% and 74.0%. In another aspect, there is provided a canola seed comprising imidazolinone resistance and oleic acid content between 74.1% and 76.0%.

In another aspect, the present invention comprises a canola hybrid seed comprising imidazolinone resistance and oleic acid content between 70.1% and 72.0%. In another aspect, the present invention comprises a canola hybrid seed comprising imidazolinone resistance and oleic acid content between 72.1% and 74.0%. In another aspect, the present invention comprises a canola hybrid seed comprising imidazolinone resistance and oleic acid content between 74.1% and 76.0%.

The present invention provides a canola seed comprising imidazolinone resistance and oleic acid content greater than 70.0% and further comprising linolenic acid content less than 3.0%. Linolenic acid is an omega-3 fatty acid also associated with heart health (Connor, W. E. (2000). Importance of n-3 fatty acids in health and disease. *Am. J. Clinical Nutrition* 71 (1 Suppl.): 171 S-5S; Brouwer I A, et al. (2004). Dietary alpha-linolenic acid is associated with reduced risk of fatal coronary heart disease, but increased prostate cancer risk: a meta-analysis. *J. Nutr.* 134 (4): 919-22. However, linolenic acid has low oxidative stability and must be at least partially hydrogenated to be shelf stable. Hydrogenation increases products' shelf life and stability, but produces trans fats (also called trans fatty acids), which several studies have linked to high cholesterol and heart disease. With growing public awareness and new laws requiring food labels to list trans fats, an alternative to hydrogenated oils is needed. In another aspect, there is provided a canola seed comprising imidazolinone resistance and oleic acid content greater than 70.0% and further comprising linolenic acid content between 2.0% and 2.99%. In another aspect, there is provided a canola seed comprising imidazolinone resistance and oleic acid content greater than 70.0% and further comprising linolenic acid content between 1.0% and 1.99. In another aspect, there is provided a canola seed comprising imidazolinone resistance and oleic acid content greater than 70.0% and further comprising linolenic acid content between 0.5% and 0.99%.

In another aspect, there is provided a canola hybrid seed comprising imidazolinone resistance and oleic acid content greater than 70.0% and further comprising linolenic acid content less than 3.0%. In another aspect, there is provided a canola hybrid seed comprising imidazolinone resistance and oleic acid content greater than 70.0% and further comprising linolenic acid content between 2.0% and 2.99%. In another aspect, there is provided a canola hybrid seed comprising imidazolinone resistance and oleic acid content greater than 70.0% and further comprising linolenic acid content between 1.0% and 1.99%. In another aspect, there is provided a canola hybrid seed comprising imidazolinone resistance and oleic acid content greater than 70.0% and further comprising linolenic acid content between 0.5% and 0.99%.

The present invention provides a canola seed comprising imidazolinone resistance and oleic acid content greater than 70.0% and less than 3.0% linolenic acid content and further comprising a canola plant with blackleg tolerance or resistance. Blackleg of canola is a serious fungal disease that can cause major yield losses in susceptible cultivars. It attacks leaves, stems and pods, and causes stem cankers, girdling and lodging. Seedlings may be killed shortly after emergence, resulting in symptoms that may be mistaken for damping-off. Infections occurring before the six leaf stage cause the most severe yield loss. The present invention also provides a hybrid canola seed comprising imidazolinone resistance and oleic acid content greater than 70.0% and less than 3.0% linolenic acid content and further comprising a canola plant with blackleg tolerance or resistance.

The present invention provides canola seeds and hybrid canola seeds with low total glucosinolate content. The glucosinolates are a class of organic compounds that contain sulfur, nitrogen and a group derived from glucose. They occur as secondary metabolites of many plants of the order Brassicales (especially in the family Brassicacea). Plants use substances derived from glucosinolates as natural pesticides and as defense against herbivores; these substances are also responsible for the bitter or sharp taste of many common foods such as mustard, horseradish, cabbage and Brussels sprouts. Many glucosinolates are poisonous to poultry and livestock. When eaten by animals or humans, glucosinolates can inhibit thyroid gland functioning, causing enlargement and atrophy of the thyroid, or goiter (Heaney R. K. et al. (1995). Natural toxins and protective factors in *Brassica* species, including rapeseed. *Natural Toxins* 3(4):233-237). Because of the bitter taste glucosinolates can impart and the possible animal poisoning that can occur, low total glucosinolate levels in canola are highly desirable. In another aspect, there is provided a canola seed comprising imidazolinone resistance and oleic acid content greater than 70.0% and total glucosinolate content of less than 12.0 μm/g of seed. In another aspect, there is provided a canola seed comprising imidazolinone resistance and oleic acid content greater than 70.0% and total glucosinolate content between 10.0 μm/g and 11.99 μm/g of seed. In another aspect, there is provided a canola seed comprising imidazolinone resistance and oleic acid content greater than 70.0% and total glucosinolate content between 8.0 μm/g and 9.99 μm/g of seed. In another aspect, there is provided a canola seed comprising imidazolinone resistance and oleic acid content greater than 70.0% and total glucosinolate content between 7.0 μm/g and 7.99 μm/g of seed.

In another aspect, there is provided a canola hybrid seed comprising imidazolinone resistance and oleic acid content greater than 70.0% and total glucosinolate content of less than 12.0 μm/g of seed. In another aspect, there is provided a canola hybrid seed comprising imidazolinone resistance and oleic acid content greater than 70.0% and total glucosinolate content between 10.0 μm/g and 11.99 μm/g of seed. In another aspect, there is provided a canola hybrid seed comprising imidazolinone resistance and oleic acid content greater than 70.0% and total glucosinolate content between 8.0 μm/g and 9.99 μm/g of seed. In another aspect, there is provided a canola hybrid seed comprising imidazolinone resistance and oleic acid content greater than 70.0% and total glucosinolate content between 7.0 μm/g and 7.99 μm/g of seed.

An array of weeds can be troublesome to canola production. Wild oats, wild buckwheat, lambsquarters, weedy mustard species and volunteer grain are some of the most common problem weeds. Canola is susceptible to significant yield reductions due to competition from weeds. In addition, seed from weedy mustard species can diminish canola oil quality with erucic acid and can also diminish canola seed meal quality with glucosinolate contamination (Dewey, S. A., S. F. Enloe, F. D. Menalled, S. D. Miller, R. E. Whitesides and L. Johnson, eds. 2006-2007 *Weed Management Handbook*, Montana, Utah, Wyoming. University of Wyoming Cooperative Extension Service. p 43-47). For these reasons, weed control in canola fields is very important. Canola plants with resistance to more than one type of herbicide offer growers the opportunity for excellent week control resulting in improved yield and improved seed quality (Upadhyay, B. M., et al. 2006. Economics of integrated weed management in herbicide-resistant canola. *Weed Science*. 54:138-147; Grichar, W. J., et al. 2006. Supplementary weed control using soil-applied herbicides in glyphosate-resistant maize in Texas. *Crop Protection* 25:1071-1074). While the plants of the present invention have resistance to imi herbicides, they can be transformed or converted by backcrossing or other breeding techniques with genes, alleles and/or events for resistance to other types of herbicides including glyphosate, glufosinate and 2, 4-D providing excellent weed control.

The canola plants of the present invention unexpectedly have a combination of high oleic acid, low linolenic acid and resistance to blackleg and imidazolinone herbicides. These characteristics are very valuable to canola growers and the food industry. The high oleic acid content and low linolenic acid content are highly desirable characteristics. The low linolenic acid content means that the oil from these plants does not have to be hydrogenated to be shelf stable. The resistance to blackleg means fewer fungicide applications and the resistance to imidazolinone means imi herbicides can be used when needed to control weeds. In addition, the seeds of the plants of the present invention have unexpectedly low total glucosinolate content.

EXAMPLES

The following examples are provided to further illustrate the present invention and are not intended to limit the invention beyond the limitations set forth in the appended claims.

Example 1

Canola Cultivar NQC02CNX12

NQC02CNX12 was developed from the cross of 45A71/Nex 705//Nex 705///Nex 715 through traditional plant breeding and the dihaploid methodology. Canola cultivar NQC02CNX12 is stable and uniform after four generations following dihaploid production and chromosome doubling and no off-type plants have been exhibited in evaluation.

NQC02CNX12 is a high oleic, low linolenic acid canola cultivar that is resistant to blackleg. Additionally, NQC02CNX12 has genes conferring tolerance to the Imidazolinone family of herbicides.

Some of the criteria used to select in various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The cultivar has been increased with continued observation for uniformity.

Canola cultivar NQC02CNX12 has the following morphologic and other characteristics (based primarily on data collected at Indianapolis, Ind.). Unexpectedly, the oleic acid content is high as well as the protein content.

TABLE 1

VARIETY DESCRIPTION INFORMATION

| | |
|---|---|
| Days to flower: | 48.5 |
| Days to maturity: | 97.1 |
| Height: | 96.5 cm |
| Lodging (1-5 scale): | 2.1 |
| Herbicide resistance: | Tolerant to Imidizolanone |
| Diseases: | Resistant to Blackleg (*Leptosphaeria maculans*) |
| Percent oil content: | 46.43% (expressed as a weight percent corrected for moisture) |
| Percent protein content: | 49.96% meal |
| Total glucosinolates: | 7.95 μmol/g seed at 8.5% moisture |
| Chlorophyll: | 31.5 mg/kg at 8.5% moisture |
| Oil profile: | |
| C18:1 (Oleic): | 71.81% |
| C18:2 (Linoleic): | 17.28% |
| C18:3 (Linolenic): | 2.40% |
| Total saturated fatty acids: | 6.50% |

In Table 2, the tolerance of NQC02CNX12 to Blackleg disease (*Leptosphaeria maculans*) is compared to other varieties of commercial canolas of similar maturity. In the table, column 1 shows the variety; columns 2 and 3 show the Blackleg disease ratings for 2002 and 2003. Column 4 lists the weighted average of the Blackleg disease ratings, column 5 gives the percent of Defender ratings, and column 6 gives the overall resistance rating using the percent of Defender value as a guideline Defender is a standard check variety for Blackleg disease ratings.

TABLE 2

BLACKLEG DISEASE RATING

| Variety | 2002 | 2003 | Wt. Avg. | % of Defender | Rating |
|---|---|---|---|---|---|
| NQC02CNX12 | 1.1 | 1.31 | 0.53 | 29 | R |
| Q2 | 2.0 | 1.36 | 1.50 | 83 | MR |
| Defender | 1.8 | 1.81 | 1.80 | 100 | MR |
| A.C. Excel | 2.3 | 2.15 | 2.20 | 121 | MS |
| Westar | 2.9 | 3.40 | 3.30 | 182 | S |
| # Trials | 1 | 4 | 5 | 5 | 5 |

In Table 3, the yield of NQC02CNX12 for the 2002-2003 long season zone is compared to other varieties of commercial canolas of similar maturity. Unexpectedly, the yield for NQC02CNX12 was higher than that of the comparison varieties. In the table, column 1 shows the variety, column 2 lists the mean yield in kilograms per hectare, and column 3 gives the percent as compared to LoLinda yield. LoLinda is a standard canola check variety.

TABLE 3

YIELD (kg/Ha) 2002-2003 Long Season Zone

| Variety | Mean Yield (kg/ha) | % of LoLinda |
|---|---|---|
| NQC02CNX12 | 2975 | 120 |
| 46A65 | 2292 | 115 |
| Q2 | 2248 | 113 |
| Ck. Avg | 2259 | 114 |
| LoLinda | 1986 | 100 |

In Table 4, the yield of NQC02CNX12 for the 2002-2003 mid-season zone is compared to other varieties of commercial canolas of similar maturity. In the table, column 1 shows the variety, column 2 shows the mean yield in kilograms per hectare and column 3 gives the percent as compared to LoLinda yield.

TABLE 4

YIELD (kg/Ha) 2002-2003 Mid-Season Zone

| Variety | Mean Yield (kg/ha) | % of LoLinda |
|---|---|---|
| NQC02CNX12 | 1954 | 113 |
| 46A65 | 1998 | 118 |
| Q2 | 1984 | 115 |
| Ck. Avg | 1001 | 115 |
| LoLinda | 1727 | 100 |

In Table 5, canola variety NQC02CNX12 is compared to other varieties of commercial canolas of similar maturity for several traits. Column 1 shows the varieties being compared, column 2 gives the days to flower, column 3 shows the days to maturity, column 4 lists the height in centimeters and column 5 shows the lodging score based on a rating of 1-5 with 1 being good (upright plants) and 5 being poor (plant fallen over).

TABLE 5

COMPARISON OF TRAITS - 2002

| Variety | Days to Flower | Days to Maturity | Height (cm) | Lodging (1-5) |
|---|---|---|---|---|
| NQC02CNX12 | 48.5 | 97.1 | 96.5 | 2.1 |
| 46A65 | 43.7 | 91.7 | 87.9 | 2.5 |
| Q2 | 46.4 | 91.5 | 88.9 | 2.3 |
| Ck. Avg | 45.1 | 91.6 | 88.0 | 2.4 |
| LoLinda | 46.0 | 92.9 | 92.3 | 2.0 |
| # Trials | 6 | 7 | 8 | 8 |

In Table 6, canola variety NQC02CNX12 is compared to other varieties of commercial canolas of similar maturity for several traits over seven trials. Unexpectedly, NQC02CNX12 has a much lower total glucosinolate content than that of the comparison varieties. Column 1 shows the varieties being compared, column 2 gives the oil content (% D.B., expressed as a weight percent corrected for moisture), column 3 shows the protein content as percent meal and column 4 lists the total glucosinolates (μmol/g seed at 8.5% moisture).

TABLE 6

COMPARISON OF TRAITS - 2002

| Variety | Oil (% D.B.) | Protein (% meal) | Total Glucosinolates μmol/g seed @ 8.5% moisture |
|---|---|---|---|
| NQC02CNX12 | 46.43 | 49.96 | 7.95 |
| 46A65 | 47.29 | 51.94 | 16.90 |
| Q2 | 46.89 | 50.13 | 13.05 |
| Ck. Avg | 47.09 | 51.04 | 14.98 |

In Table 7, canola variety NQC02CNX12 is compared to other varieties of commercial canolas of similar maturity for several fatty acids. Unexpectedly, NQC02CNX12 had a significantly higher oleic acid content and a significantly lower linolenic content than those of the comparison varieties. Column 1 shows the varieties being compared, columns 2-4 show the percent of C18:1, C18:2 and C18:3 and column 5 show the percent total saturated fatty acids.

TABLE 7

COMPARISON OF OIL TRAITS - 2002

| Variety | C18:1 | C18:2 | C18:3 | TOTSAT |
|---|---|---|---|---|
| NQC02CNX12 | 71.81 | 17.28 | 2.40 | 6.50 |
| 46A65 | 63.30 | 19.30 | 8.69 | 6.57 |
| Q2 | 63.03 | 18.16 | 9.73 | 6.91 |
| LoLinda | 64.47 | 23.82 | 3.27 | 6.38 |

In Table 8 that follows, the FAME Analysis of canola variety NQC02CNX12 is given. In the table, column 1 shows the type of fat while column 2 shows the percent of total oil of each type of fat found in the cultivar.

TABLE 8

FAME Analysis - % of Total Oil
NQC02CNX12

| Oil | % of Total Oil |
|---|---|
| C12:0 | 0.02 |
| C14:0 | 0.06 |
| C16:0 | 3.48 |
| C16:1 | 0.41 |
| C18:0 | 1.73 |
| C18:1 | 71.95 |
| C18:2 | 16.86 |
| C18:3 | 1.94 |
| C20:0 | 0.58 |
| C20:1 | 1.25 |
| C20:2 | 0.09 |
| C22:0 | 0.31 |
| C22:1 | 0.02 |
| C24:0 | 0.22 |
| C24:1 | 0.19 |
| Totsat | 6.37 |

Example 2

Canola Cultivar NQC02CNX25

NQC02CNX25 was developed from the cross of 45A71/Nex 705//Nex 705///Nex 715 through traditional plant breeding and the dihaploid methodology. Canola cultivar NQC02CNX25 is stable and uniform after four generations following dihaploid production and chromosome doubling and no off-type plants have been exhibited in evaluation.

NQC02CNX25 is a high oleic, low linolenic acid canola cultivar that is resistant to blackleg. Additionally, NQC02CNX25 has genes conferring tolerance to the Imidazolinone family of herbicides.

Some of the criteria used to select in various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The cultivar has been increased with continued observation for uniformity.

Canola cultivar NQC02CNX25 has the following morphologic and other characteristics (based primarily on data collected at Indianapolis, Ind.). Unexpectedly, the oleic acid content was high and the protein content was also high.

TABLE 9

VARIETY DESCRIPTION INFORMATION

| | |
|---|---|
| Days to flower: | 48.1 |
| Days to maturity: | 93.8 |
| Height: | 97.6 cm |
| Lodging (1-5 scale): | 2 |
| Herbicide resistance: | Tolerant to Imidizolanone |
| Diseases: | Resistant to Blackleg (*Leptosphaeria maculans*) |
| Percent oil content: | 45.26% (expressed as a weight percent corrected for moisture) |
| Percent protein content: | 54.82% meal |
| Total glucosinolates: | 11.00 μmol/g seed at 8.5% moisture |
| Chlorophyll: | 14.4 mg/kg at 8.5% moisture |
| Oil profile: | |
| C18:1: | 71.44% |
| C18:2: | 17.50% |
| C18:3: | 2.58% |
| Total saturated fatty acids: | 6.34% |

In Table 10, the tolerance of NQC02CNX25 to Blackleg disease (*Leptosphaeria maculans*) is compared to other varieties of commercial canolas of similar maturity. In the table, column 1 shows the variety, columns 2 and 3 show the Blackleg disease ratings for 2002 and 2003. Blackleg disease ratings are based on a 1-5 scale with 1 being resistant and 5 being susceptible. Column 4 lists the weighted average, column 5 gives the percent of Defender ratings and column 6 gives the overall resistance rating using the percent of Defender value as a guideline.

TABLE 10

COMPARISON OF TOLERANCE TO BLACKLEG DISEASE

| Variety | 2002 | 2003 | Wt. Avg. | % of Defender | Rating |
|---|---|---|---|---|---|
| NQC02CNX25 | 0.85 | 1.31 | 0.76 | 42 | R |
| Q2 | 2.0 | 1.36 | 1.50 | 83 | MR |
| Defender | 1.8 | 1.81 | 1.80 | 100 | MR |
| A.C. Excel | 2.3 | 2.15 | 2.20 | 121 | MS |
| Westar | 2.9 | 3.40 | 3.30 | 182 | S |
| # Trials | 1 | 4 | 5 | 5 | 5 |

In Table 11, the yield of NQC02CNX25 for the 2002-2003 long season zone is compared to other varieties of commercial canolas of similar maturity. Unexpectedly, the yield of NQC02CNX25 was significantly higher than that of the comparison varieties. In the table, column 1 shows the variety, column 2 shows the mean yield in kilograms per hectare, and column 3 shows the percent as compared to LoLinda yield.

TABLE 11

YIELD (kg/Ha) 2002-2003 Long Season Zone

| Variety | Mean Yield (kg/ha) | % of LoLinda |
|---|---|---|
| NQC02CNX25 | 2381 | 120 |
| 46A65 | 2292 | 115 |
| Q2 | 2248 | 113 |
| Ck. Avg | 2259 | 114 |
| LoLinda | 1986 | 100 |

In Table 12 that follows, the yield of NQC02CNX25 for the 2002-2003 mid-season zone is compared to other varieties of commercial canolas of similar maturity. In the table, column 1 shows the variety, column 2 lists the mean yield in kilograms per hectare and column 3 gives the percent as compared to LoLinda yield.

TABLE 12

YIELD (kg/Ha) 2002-2003 Mid-Season Zone

| Variety | Mean Yield (kg/ha) | % of LoLinda |
|---|---|---|
| NQC02CNX25 | 1873 | 108 |
| 46A65 | 1998 | 118 |
| Q2 | 1984 | 115 |
| Ck. Avg | 1001 | 115 |
| LoLinda | 1727 | 100 |

In Table 13, canola variety NQC02CNX25 is compared to other varieties of commercial canolas of similar maturity for several traits. Column 1 shows the varieties being compared, column 2 gives the days to flower, column 3 shows the days to maturity, column 4 lists the height in centimeters and column 5 shows the lodging score based on 1-5 with 1 being good (upright plants) and 5 being poor (plant fallen over).

TABLE 13

COMPARISON OF TRAITS - 2002

| Variety | Days to Flower | Days to Maturity | Height (cm) | Lodging (1-5) |
|---|---|---|---|---|
| NQC02CNX25 | 48.1 | 93.8 | 97.6 | 2.0 |
| 46A65 | 43.7 | 91.7 | 87.9 | 2.5 |
| Q2 | 46.4 | 91.5 | 88.9 | 2.3 |
| Ck. Avg | 45.1 | 91.6 | 88.0 | 2.4 |
| LoLinda | 46.0 | 92.9 | 92.3 | 2.0 |
| # Trials | 6 | 7 | 8 | 8 |

In Table 14, canola variety NQC02CNX25 is compared to other varieties of commercial canolas of similar maturity for several traits over seven trials. Column 1 shows the varieties being compared, column 2 shows the Oil content (% D.B.—oil content expressed as a weight percent corrected for moisture), column 3 shows the percent protein content as percent meal, and column 4 shows the total glucosinolates (μmol/g seed at 8.5% moisture).

TABLE 14

COMPARISON OF TRAITS - 2002

| Variety | Oil (% D.B.) | Protein (% meal) | Total Glucosinolates μmole/g seed @ 8.5% moisture |
|---|---|---|---|
| NQC02CNX25 | 45.26 | 54.82 | 11.00 |
| 46A65 | 47.29 | 51.94 | 16.90 |
| Q2 | 46.89 | 50.13 | 13.05 |
| Ck. Avg | 47.09 | 51.04 | 14.98 |

In Table 15, canola variety NQC02CNX25 is compared to other varieties of commercial canolas of similar maturity for several fatty acids. Column 1 shows the varieties being compared, columns 2-4 show the percent of C18:1, C18:2 and C18:3 and column 5 show the percent total saturated fatty acids. Unexpectedly, the oleic acid content was significantly higher and the linolenic content was significantly lower for NQC02CNX25 than those of the comparison varieties.

TABLE 15

COMPARISON OF OIL TRAITS - 2002

| Variety | C18:1 | C18:2 | C18:3 | TOTSAT |
|---|---|---|---|---|
| NQC02CNX25 | 71.44 | 17.50 | 2.58 | 6.34 |
| 46A65 | 63.30 | 19.30 | 8.69 | 6.57 |
| Q2 | 63.03 | 18.16 | 9.73 | 6.91 |
| LoLinda | 64.47 | 23.82 | 3.27 | 6.38 |

In Table 16 that follows, the FAME Analysis of canola variety NQC02CNX25 is given. In the table, column 1 shows the type of fat while column 2 shows the percent of total oil of each type of fat found in the cultivar.

TABLE 16

Fame Analysis - % Total Oil

| Oil | NQC02CNX25 |
|---|---|
| C12:0 | 0.01 |
| C14:0 | 0.05 |
| C16:0 | 3.53 |
| C16:1 | 0.29 |
| C18:0 | 1.61 |
| C18:1 | 73.38 |
| C18:2 | 15.52 |
| C18:3 | 1.82 |
| C20:0 | 0.56 |
| C20:1 | 1.45 |
| C20:2 | 0.07 |
| C22:0 | 0.32 |
| C22:1 | 0.03 |
| C24:0 | 0.18 |
| C24:1 | 0.13 |
| Totsat | 6.26 |

Example 3

Canola Cultivar NQC02CNX21

NQC02CNX21 was developed from the cross of 45A71/Nex 705//Nex 705///Nex 715 through traditional plant breeding and the dihaploid methodology. Canola cultivar is stable and uniform after four generations following dihaploid production and chromosome doubling and no off-type plants have been exhibited in evaluation.

NQC02CNX21 is a high oleic, low linolenic acid canola line that is resistant to blackleg and white rust. Additionally, NQC02CNX21 has genes conferring tolerance to the Imidazolinone family of herbicides.

Some of the criteria used to select in various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The line has been increased with continued observation for uniformity.

Canola cultivar NQC02CNX21 has the following morphologic and other characteristics based primarily on data collected in the Western Canadian provinces and in Indianapolis, Ind. Unexpectedly, the protein content of NQC02CNX21 was high as well as the oleic acid content.

TABLE 17

VARIETY DESCRIPTION INFORMATION

| | |
|---|---|
| Days to Flower: | 47.7 |
| Days to Maturity: | 94.6 |
| Height: | 110 cm |
| Lodging Resistance: | 1.9 |
| Yield, Long Season Zone: | 2535 kg/ha |
| Yield, Mid-Season Zone: | 2561 kg/ha |
| Percent oil content: | 45.3% (expressed as a weight percent corrected for moisture) |
| Percent protein content: | 48.7% meal |
| Total glucosinolates: | 9.4 μm/g seed at 8.5% moisture |
| Chlorophyll: | 18.9 mg/kg at 8.5% moisture |
| Oil Profile: | |
| C18:1: | 72.21 |
| C18:2: | 17.98 |
| C18:3: | 1.78 |
| Total Saturated Fatty Acid: | 5.92% |
| Disease Reactions: | |
| Blackleg (Leptosphaeria maculans): | Resistant |
| White Rust (Albugo candida): | Resistant |
| Herbicide Reactions: Imidazolinones | Resistant |

In Table 18, the tolerance of NQC02CNX21 to Blackleg disease (Leptosphaeria maculans) is compared to other varieties of commercial canolas of similar maturity. In the table, column 1 shows the variety; columns 2 and 3 are the Blackleg disease rating for 2002 and 2003. Blackleg disease ratings are based on a 1-5 scale of 1 being resistant and 5 being susceptible. Column 4 lists the weighted average; column 5 gives the percent of Defender ratings; and column 6 gives the overall resistance rating using the percent of Defender value as a guideline.

TABLE 18

BLACKLEG DISEASE

| Variety | 2002 | 2003 | Wt. Avg. | % of Defender | Rating |
|---|---|---|---|---|---|
| NQC02CNX21 | 0.95 | 1.31 | 1.01 | 56 | R |
| Q2 | 2.0 | 1.36 | 1.50 | 83 | MR |
| Defender | 1.8 | 1.81 | 1.80 | 100 | MR |
| A.C. Excel | 2.3 | 2.15 | 2.20 | 121 | MS |
| Westar | 2.9 | 3.40 | 3.30 | 182 | S |
| # Trials | 1 | 4 | 5 | 5 | 5 |

In Table 19, the tolerance of NQC02CNX21 to White Rust (Albugo candida) is compared to other varieties of commercial canolas of similar maturity. In the Table, column 1 shows the variety and column 2 shows the percentage of plants infected by Race 7V of the disease.

TABLE 19

Percent Infection with White Rust Race 7V

| Variety | Race 7V Infection (%) |
|---|---|
| NQC02CNX21 | 1 |
| Horizon | 100 |
| Tobin | 99 |
| Commercial Brown Mustard | 0 |

In Table 20, the tolerance of NQC02CNX21 to White Rust (*Albugo candida*) is compared to other varieties of commercial canolas of similar maturity. In the Table, column 1 shows the variety and column 2 shows the percentage of plants infected by Race 2V of the disease.

TABLE 20

Percent Infection with White Rust Race 2V

| Variety | Race 2V Infection (%) |
|---|---|
| NQC02CNX21 | 0 |
| Horizon | 0 |
| Cutlass | 97 |
| Commercial Brown Mustard | 100 |

In Table 21, the yield of NQC02CNX21 for the 2002-2003 long season zone is compared to other varieties of commercial canolas of similar maturity. Unexpectedly, the yield of NQC02CNX21 was significantly higher than that of the comparison varieties. In the table, column 1 shows the variety; column 2 lists the mean yield in kilograms per hectare. Column 3 gives the percent as compared to LoLinda yield.

TABLE 21

YIELD (kg/Ha) 2002-2003 Long Season Zone

| Variety | Mean Yield (kg/ha) | % of LoLinda |
|---|---|---|
| NQC02CNX21 | 2535 | 140 |
| 46A65 | 2234 | 123 |
| Q2 | 2247 | 124 |
| Ck. Avg | 2240 | 123 |
| LoLinda | 1817 | 100 |
| CV (%) | 9.0 | |

In Table 22, the yield of NQC02CNX21 for the 2002-2003 mid-season zone is compared to other varieties of commercial canolas of similar maturity. Unexpectedly, the yield of NQC02CNX21 was significantly higher than that of the comparison varieties. In the table, column 1 shows the variety; column 2 lists the mean yield in kilograms per hectare. Column 3 gives the percent as compared to LoLinda yield.

TABLE 22

YIELD (kg/Ha) 2002-2003 Mid-Season Zone

| Variety | Mean Yield (kg/ha) | % of LoLinda |
|---|---|---|
| NQC02CNX21 | 2561 | 136 |
| 46A65 | 2226 | 118 |
| Q2 | 2099 | 111 |
| Ck. Avg | 2163 | 115 |

TABLE 22-continued

YIELD (kg/Ha) 2002-2003 Mid-Season Zone

| Variety | Mean Yield (kg/ha) | % of LoLinda |
|---|---|---|
| LoLinda | 1886 | 100 |
| CV (%) | 11 | |

In Table 23, canola variety NQC02CNX21 is compared to other varieties of commercial canolas of similar maturity for several traits. Column 1 shows the variety being compared; column 2 gives the days to flower; column 3 shows the days to maturity; column 4 lists the height in centimeters and column 5 shows the lodging score based on 1-5, 1 being good (upright plants) and 5 being poor (plant fallen over).

TABLE 23

COMPARISON OF TRAITS - 2002

| Variety | Days to Flower | Days to Maturity | Height (cm) | Lodging (1-5) |
|---|---|---|---|---|
| NQC02CNX21 | 47.7 | 94.6 | 110 | 1.9 |
| 46A65 | 43.6 | 89.4 | 96 | 2.2 |
| Q2 | 46.2 | 89.8 | 99 | 2.1 |
| Ck. Avg | 44.9 | 89.6 | 98 | 2.2 |
| LoLinda | 45.9 | 90.7 | 102 | 1.8 |
| # Trials | 16 | 16 | 17 | 16 |

In Table 24, canola variety NQC02CNX21 is compared to other varieties of commercial canolas of similar maturity for several traits. Unexpectedly, the total glucosinolate content of NQC02CNX21 was significantly lower than that of the comparison varieties. Column 1 shows the variety being compared; column 2 gives the percent oil % D.B. (oil content expressed as a weight percent corrected for moisture); column 3 shows the percent protein content as percent meal); column 4 lists the total glucosinolates ($\mu$m/g seed at 8.5% moisture) and column 5 shows the chlorophyll content (kg at 8.5% moisture).

TABLE 24

COMPARISON OF TRAITS - 2002

| Variety | Oil (% D.B.) | Protein (% meal) | Total Glucosinolates $\mu$m/g seed @ 8.5% moisture | Chlorophyll mg/kg @ 8.5% moisture |
|---|---|---|---|---|
| NQC02CNX21 | 45.3 | 48.7 | 9.4 | 18.9 |
| 46A65 | 46.2 | 48.3 | 15.8 | |
| Q2 | 45.1 | 48.3 | 12.6 | |
| Ck. Avg | 45.7 | 48.3 | 14.2 | |
| LoLinda | 43.9 | 48.1 | | |
| # Trials | 15 | 15 | 11 | 8 |

In Table 25, the C18 oil profile of canola variety NQC02CNX21 is compared to other varieties of commercial canolas of similar maturity. In the Table, column 1 shows the variety, columns 2-4 show the percentage of C18:1, C18:2, and C18:3 respectively, while column 5 shows the total saturated fatty acid.

TABLE 25

C18 and Total Saturated Fatty Acid Profile for NQC02CNX21

| Variety | C18:1 | C18:2 | 18:3 | TOTSAT |
|---|---|---|---|---|
| NQC02CNX21 | 71.33 | 17.89 | 0.96 | 0.49 |
| 46A65 | 64.56 | 18.45 | 0.41 | 0.90 |
| Q2 | 63.96 | 17.84 | 0.18 | 0.09 |
| Check | 64.26 | 18.15 | 0.80 | 0.00 |
| LoLinda | 64.55 | 23.29 | 0.80 | 0.63 |

Table 26 provides the FAME analysis for canola cultivar NQC02CNX21. In the Table, column 1 shows the type of fat while column 2 shows the percent of total oil of each type of fat found in the cultivar.

TABLE 26

FAME Analysis

| Oil | NQC02CNX21 |
|---|---|
| C12:0 | 0.01 |
| C14:0 | 0.05 |
| C16:0 | 3.63 |
| C16:1 | 0.25 |
| C18:0 | 1.31 |
| C18:1 | 72.21 |
| C18:2 | 17.98 |
| C18:3 | 1.78 |
| C20:0 | 0.49 |
| C20:1 | 1.55 |
| C20:2 | 0.08 |
| C22:0 | 0.31 |
| C22:1 | nd |
| C24:0 | 0.13 |
| C24:1 | 0.24 |
| TOTSAT | 5.92 |

Example 4

Canola Cultivar NQC02CNX13

NQC02CNX13 was developed from the cross of 45A71/Nex 705//Nex 705///Nex 715 through traditional plant breeding and the dihaploid methodology. Canola cultivar NQC02CNX13 is stable and uniform after four generations following dihaploid production and chromosome doubling and no off-type plants have been exhibited in evaluation.

NQC02CNX13 is a high oleic, low linolenic acid canola line that is resistant to blackleg and white rust. Additionally, NQC02CNX13 has genes conferring tolerance to the Imidazolinone family of herbicides.

Some of the criteria used to select in various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The line has been increased with continued observation for uniformity.

Canola cultivar NQC02CNX13 has the following morphologic and other characteristics based primarily on data collected in the Western Canadian provinces and in Indianapolis, Ind.

TABLE 27

VARIETY DESCRIPTION INFORMATION

| | |
|---|---|
| Days to flower: | 49.3 |
| Days to maturity: | 93.9 |
| Height: | 111 cm |
| Lodging Score: | 1.5 |
| Yield, long season zone: | 2273 kg/ha |
| Yield, mid-season zone: | 2277 kg/ha |
| Percent oil content: | 44.2% (expressed as a weight percent corrected for moisture) |
| Percent protein content: | 47.3% meal |
| Total glucosinolates: | 10.1 µm/g at 8.5% moisture |
| Chlorophyll: | 16.8 mg/kg at 8.5% moisture |
| Oil profile: | |
| C18:1: | 75.25 |
| C18:2: | 14.49 |
| C18:3: | 1.81 |
| Total saturated fatty acids: | 6.44% |
| Disease Reactions: | |
| White Rust (*Albugo candida*): | Resistant |
| Blackleg (*Leptosphaeria maculans*): | Resistant |
| Herbicide Reactions: Imidazolinones: | Resistant |

In Table 28, the tolerance of NQC02CNX13 to Blackleg disease (*Leptosphaeria maculans*) is compared to other varieties of commercial canolas of similar maturity. In the table, column 1 shows the variety; columns 2 and 3 are the Blackleg disease rating for 2002 and 2003. Blackleg disease ratings are based on a 1-5 scale of 1 being resistant and 5 being susceptible. Column 4 lists the weighted average; column 5 gives the percent of Defender ratings; and column 6 gives the overall resistance rating using the percent of Defender value as a guideline.

TABLE 28

BLACKLEG DISEASE

| Variety | 2002 | 2003 | Wt. Avg. | % of Defender | Rating |
|---|---|---|---|---|---|
| NQC02CNX13 | 1.3 | 1.31 | 1.01 | 56 | R |
| Q2 | 2.0 | 1.36 | 1.50 | 83 | MR |
| Defender | 1.8 | 1.81 | 1.80 | 100 | MR |
| A.C. Excel | 2.3 | 2.15 | 2.20 | 121 | MS |
| Westar | 2.9 | 3.40 | 3.30 | 182 | S |
| # Trials | 1 | 4 | 5 | 5 | 5 |

In Table 29, the tolerance of NQC02CNX13 to White Rust (*Albugo candida*) is compared to other varieties of commercial canolas of similar maturity. In the Table, column 1 shows the variety and column 2 shows the percentage of plants infected by Race 7V of the disease.

TABLE 29

Percent Infection with Race 7V

| Variety | Race 7V Infection (%) |
|---|---|
| NQC02CNX13 | 0 |
| Horizon | 98 |
| Tobin | 100 |
| Commercial Brown Mustard | 0 |

In Table 30, the tolerance of NQC02CNX13 to White Rust (*Albugo candida*) is compared to other varieties of commercial canolas of similar maturity. In the Table, column 1 shows the variety and column 2 shows the percentage of plants infected by Race 2V of the disease.

TABLE 30

Percent Infection with Race 2V

| Variety | Race 2V Infection (%) |
|---|---|
| NQC02CNX13 | 0 |
| Torch | 1 |
| Cutlass | 96 |
| Commercial Brown Mustard | 100 |

In Table 31, the yield of NQC02CNX13 for the 2002-2003 long season zone is compared to other varieties of commercial canolas of similar maturity. In the table, column 1 shows the variety; column 2 lists the mean yield in kilograms per hectare. Column 3 gives the percent as compared to LoLinda yield.

TABLE 31

YIELD (kg/Ha) 2002-2003 Long-Season Zone

| Variety | Mean Yield | % of LoLinda |
|---|---|---|
| NQC02CNX13 | 2273 | 125 |
| 46A65 | 2234 | 123 |
| Q2 | 2247 | 124 |
| Ck. Avg | 2240 | 123 |
| LoLinda | 1817 | 100 |
| CV (%) | 9.0 | |

In Table 32, the yield of NQC02CNX13 for the 2002-2003 mid-season zone is compared to other varieties of commercial canolas of similar maturity. In the table, column 1 shows the variety; column 2 lists the mean yield in kilograms per hectare. Column 3 gives the percent as compared to LoLinda yield.

TABLE 32

YIELD (kg/Ha) 2002-2003 Mid-Season Zone

| Variety | Mean Yield (kg/ha) | % of LoLinda |
|---|---|---|
| NQC02CNX13 | 2277 | 121 |
| 46A65 | 2226 | 118 |
| Q2 | 2099 | 111 |
| Ck. Avg | 2163 | 115 |
| LoLinda | 1886 | 100 |
| CV (%) | 11 | |

In Table 33, canola variety NQC02CNX13 is compared to other varieties of commercial canolas of similar maturity for several traits. Column 1 shows the variety being compared; column 2 gives the days to flower; column 3 shows the days to maturity; column 4 lists the height in centimeters and column 5 shows the lodging score based on 1-5, 1 being good (upright plants) and 5 being poor (plant fallen over).

TABLE 33

COMPARISON OF TRAITS - 2002-2003

| Variety | Days to Flower | Days to Maturity | Height (cm) | Lodging (1-5) |
|---|---|---|---|---|
| NQC02CNX13 | 49.3 | 93.9 | 111 | 1.5 |
| 46A65 | 43.6 | 89.4 | 96 | 2.2 |
| Q2 | 46.2 | 89.8 | 99 | 2.1 |
| Ck. Avg | 44.9 | 89.6 | 98 | 2.2 |
| LoLinda | 45.9 | 90.7 | 102 | 1.8 |
| # Trials | 16 | 16 | 17 | 16 |

In Table 34, canola variety NQC02CNX13 is compared to other varieties of commercial canolas of similar maturity for several traits. Unexpectedly, the total glucosinolate content of NQC02CNX13 was significantly lower than that of the comparison varieties. Column 1 shows the variety being compared; column 2 gives the percent oil content % D.B. (oil content expressed as a weight percent corrected for moisture); column 3 shows the percent protein content as percent meal); column 4 lists the total glucosinolates (μm/g seed@8.5% moisture) and column 5 shows the chlorophyll content (kg at 8.5% moisture).

TABLE 34

COMPARISON OF TRAITS - 2002

| Variety | Oil (% D.B.) | Protein (% meal) | Total Glucosinolates μm/g seed @ 8.5% moisture | Chlorophyll mg/kg @ 8.5% moisture |
|---|---|---|---|---|
| NQC02CNX13 | 44.2 | 47.3 | 10.1 | 16.8 |
| 46A65 | 46.2 | 48.3 | 15.8 | |
| Q2 | 45.1 | 48.3 | 12.6 | |
| Ck. Avg | 45.7 | 48.3 | 14.2 | |
| LoLinda | 43.9 | 48.1 | | |
| # Trials | 15 | 15 | 11 | 8 |

In Table 35, the C18 oil profile of canola variety NQC02CNX13 is compared to other varieties of commercial canolas of similar maturity. Unexpectedly, the oleic acid content was significantly higher and the linolenic acid content was significantly lower for NQC02CNX13 than those of the comparison varieties. In the Table, column 1 shows the variety, columns 2-4 show the percentage of C18:1, C18:2, and C18:3 respectively, while column 5 shows the total saturated fatty acid.

TABLE 35

C18 and Total Saturated Fatty Acid Profile

| Variety | C18:1 | C18:2 | 18:3 | TOTSAT |
|---|---|---|---|---|
| NQC02CNX13 | 74.76 | 13.77 | 1.84 | 6.73 |
| 46A65 | 64.56 | 18.45 | 7.41 | 6.90 |
| Q2 | 63.96 | 17.84 | 8.18 | 7.09 |
| Check | 64.26 | 18.15 | 7.80 | 7.00 |
| LoLinda | 64.55 | 23.29 | 2.80 | 6.63 |

Table 36 provides the FAME analysis for canola cultivar NQC02CNX13. In the Table, column 1 shows the type of fat while column 2 shows the percent of total oil of each type of fat found in the cultivar.

TABLE 36

FAME Analysis

| Oil | NQC02CNX13 |
|---|---|
| C12:0 | nd |
| C14:0 | 0.05 |
| C16:0 | 3.47 |
| C16:1 | 0.24 |
| C18:0 | 1.75 |
| C18:1 | 75.25 |
| C18:2 | 14.49 |
| C18:3 | 1.81 |
| C20:0 | 0.60 |
| C20:1 | 1.47 |
| C20:2 | 0.06 |
| C22:0 | 0.35 |

TABLE 36-continued

FAME Analysis

| Oil | NQC02CNX13 |
|---|---|
| C22:1 | nd |
| C24:0 | 0.23 |
| C24:1 | 0.25 |
| TOTSAT | 6.44 |

Example 5

Canola Cultivar NQC03CNX01

NQC03CNX01 is a high oleic, low linolenic acid canola line that is resistant to blackleg and white rust. Additionally, NQC03CNX01 has genes conferring tolerance to the Imidazolinone family of herbicides.

Canola cultivar NQC03CNX01 has the following morphologic and other characteristics based primarily on data collected in the Western Canadian provinces and in Indianapolis, Ind.

TABLE 37

VARIETY DESCRIPTION INFORMATION

| Days to flower: | 49.3 |
|---|---|
| Days to maturity: | 93.6 |
| Height: | 111 cm |
| Lodging Score: | 1.5 |
| Yield: | 90% of standard commercial canola cultivar 46A65 |
| Percent oil content: | 44.75% (expressed as a weight percent corrected for moisture) |
| Percent protein content: | 46.5% meal |
| Total glucosinolates: | 11.92 μm/g at 8.5% moisture |
| Oil profile: | |
| C18:1: | 73.11 |
| C18:2: | 14.63 |
| C18:3: | 2.00 |
| Total saturated fatty acids: | 6.69% |
| Disease Reactions: | |
| White Rust (*Albugo candida*): | Resistant |
| Blackleg (*Leptosphaeria maculans*): | Resistant |
| Herbicide Reactions: Imidazolinones: | Resistant |

Example 6

Canola Cultivar NQC02CNX10

NQC02CNX10 is a high oleic, low linolenic acid canola line that is resistant to white rust and moderately resistant to blackleg. Additionally, NQC02CNX10 has genes conferring tolerance to the Imidazolinone family of herbicides.

Canola cultivar NQC02CNX10 has the following morphologic and other characteristics based primarily on data collected in the Western Canadian provinces and in Indianapolis, Ind.

TABLE 38

VARIETY DESCRIPTION INFORMATION

| Days to flower: | 47.6 |
|---|---|
| Days to maturity: | 93.2 |
| Height: | 104 cm |
| Lodging Score: | 1.7 |

TABLE 38-continued

VARIETY DESCRIPTION INFORMATION

| Yield: | 99% of standard commercial canola cultivar 46A65 |
|---|---|
| Percent oil content: | 47.01% (expressed as a weight percent corrected for moisture) |
| Percent protein content: | 49.15% meal |
| Total glucosinolates: | 10.47 μm/g at 8.5% moisture |
| Chlorophyll: | 11.17 mg/kg at 8.5% moisture |
| Oil profile: | |
| C18:1: | 73.32 |
| C18:2: | 15.93 |
| C18:3: | 2.30 |
| Total saturated fatty acids: | 6.50% |
| Disease Reactions: | |
| White Rust (*Albugo candida*): | Resistant |
| Blackleg (*Leptosphaeria maculans*): | Moderately Resistant |
| Herbicide Reactions: Imidazolinones: | Resistant |

Example 7

Canola Cultivar NQC02CNX20

NQC02CNX20 is a high oleic, low linolenic acid canola line that is resistant to blackleg and white rust. Additionally, NQC02CNX20 has genes conferring tolerance to the Imidazolinone family of herbicides.

Canola cultivar NQC02CNX20 has the following morphologic and other characteristics based primarily on data collected in the Western Canadian provinces and in Indianapolis, Ind.

TABLE 39

VARIETY DESCRIPTION INFORMATION

| Days to flower: | 50.5 |
|---|---|
| Days to maturity: | 94.6 |
| Height: | 110 cm |
| Lodging Score: | 1.6 |
| Yield: | 92% of standard commercial canola cultivar 46A65 |
| Percent oil content: | 46.14% (expressed as a weight percent corrected for moisture) |
| Percent protein content: | 48.80% meal |
| Total glucosinolates: | 8.21 μm/g at 8.5% moisture |
| Chlorophyll: | 13 mg/kg at 8.5% moisture |
| Oil profile: | |
| C18:1: | 73.32 |
| C18:2: | 15.93 |
| C18:3: | 2.30 |
| Total saturated fatty acids: | 6.50% |
| Disease Reactions: | |
| White Rust (*Albugo candida*): | Resistant |
| Blackleg (*Leptosphaeria maculans*): | Moderately Resistant |
| Herbicide Reactions: Imidazolinones: | Resistant |

Further Embodiments Of The Invention

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed canola plants, using transformation methods as described below to incorporate transgenes into the genetic material of the canola plant(s).

Expression Vectors for Canola Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, which when under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase and the bleomycin resistance determinant. Hayford et al., *Plant Physiol.* 86:1216 (1988), Jones et al., *Mol. Gen. Genet*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci. U.S.A.* 84:131 (1987), DeBlock et al., *EMBO J.* 3:1681 (1984).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as selectable markers.

Expression Vectors for Canola Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in canola. Optionally, the inducible promoter is operably linked to a nucleotide sequence encoding a signal sequence which is operably linked to a gene for expression in canola. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); In2 gene from maize which responds to benzenesulfonamide herbicide safeners (Hershey et al., *Mol. Gen. Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters—A constitutive promoter is operably linked to a gene for expression in canola or the constitutive promoter is operably linked to a nucleotide sequence encoding a signal sequence which is operably linked to a gene for expression in canola.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in canola. Optionally, the tissue-specific promoter is operably linked to a nucleotide sequence encoding a signal sequence which is operably linked to a gene for expression in canola. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a canola plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (Arabidopsis RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi-4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. See also Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995).

U. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2): 137-149 (1998).

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., *Theor. Appl. Genet.* 80:449 (1990), respectively.

B. Glyphosate (GOX, GT73/RT73, DMMG, MD-1 and MD-12 genes) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. Nos. 5,633,435 and 5,804,425 to Barry et al., which disclose class II 5-enolpyruvylshikimate-3-phosphate synthase (EPSPS) enzymes which confer tolerance to glyphosate herbicides.

Glyphosate-tolerant canola line GT73 was produced by the method of the Barry et al. patents as a result of the transfer of the following genes: the CP4-EPSPS gene from *Agrobacterium* sp. strain CP4 under the control of the modified figwort mosaic virus 35S promoter and the glyphosate oxidoreductase (gox) gene from *Ochromobactrum anthropii* strain LBM [previously *Achromobacter* sp] also under the control of the modified figwort mosaic virus 35S promoter. The gene encodes the GOXv247 variant protein. An example of an ESPS mutant which confers tolerance to glyphosate herbicides is the DMMG gene described by Lebrun et al. in U.S. Pat. No. 6,566,587.

In addition to genes which confer tolerance to glyphosate herbicides, there are also genes which confer tolerance to auxin herbicides. For example, see international publication WO 2005/107437 which discloses the AAD-1 gene which confers resistance to phenoxy auxins (2, 4-D, MCPA, Mecoprop, Dichlorprop) and aryloxyalkanoate herbicides (fluazifop, haloxyfop, quizalofop, cyhalofop, etc). Also see international publication WO 2007/053482 which discloses the AAD-12 gene which confers resistance to phenoxy auxins (2, 4-D, MCPA, Mecoprop, Dichlorprop) and pyridyloxy auxin herbicides (fluoroxypyr and triclopyr).

Additionally, see, for example, U.S. Pat. No. 4,975,374 to Goodman et al., which discloses the sequences of glutamine synthetase genes which confer resistance to herbicides such as L-phosphinothricin. The sequence of a PAT gene is provided in European application No. 0 242 246 to Leemans et al., while DeGreef et al., *Bio/Technology* 7:61 (1989), describe the production of transgenic plants that express chimeric bar genes coding for PAT activity. Further examples of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767, 373; and international publication WO 01/12825.

3. Genes That Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content-1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., Bio/Technology 10:292 (1992) (production of transgenic plants that express *Bacillus licheniformis* α-amylase), Elliot et al., Plant Molec. Biol. 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

Methods for Canola Transformation

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*

10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of canola target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular canola line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture

Further production of a high oleic, low linolenic canola cultivar can occur by self-pollination or by tissue culture and regeneration. Tissue culture of various tissues of canola and regeneration of plants therefrom is well-known and widely published. For example, the propagation of a canola cultivar by tissue culture is described in any of the following, but not limited to any of the following: Chuong et al., "A Simple Culture Method for *Brassica* hypocotyls Protoplasts", *Plant Cell Reports* 4:4-6 (1985); Barsby, T. L., et al., "A Rapid and Efficient Alternative Procedure for the Regeneration of Plants from Hypocotyl Protoplasts of *Brassica napus*", *Plant Cell Reports*, (Spring, 1996); Kartha, K., et al., "In vitro Plant Formation from Stem Explants of Rape", *Physiol. Plant,* 31:217-220 (1974); Narasimhulu, S., et al., "Species Specific Shoot Regeneration Response of Cotyledonary Explants of Brassicas", *Plant Cell Reports*, (Spring 1988); Swanson, E., "Microspore Culture in *Brassica*", *Methods in Molecular Biology*, Vol. 6, Chapter 17, p. 159 (1990). Thus, another aspect of this invention is to provide cells which upon growth and differentiation produce canola plants having the physiological and morphological characteristics of canola variety NQC02CNX21.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, pistils, anthers, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, described certain techniques, the disclosures of which are incorporated herein by reference.

Single Gene Converted (Conversion) Plants

When the term "canola plant" is used in the context of the present invention, this also includes any single gene conversions of that variety. The term "single gene converted plant" as used herein refers to those canola plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental canola plant which contributes the gene for the desired characteristic is termed the "nonrecurrent" or "donor parent". This terminology refers to the fact that the nonrecurrent parent is used one time in the backcross protocol and therefore does not recur. The parental canola plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a canola plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

Additional Breeding Methods

This invention also is directed to methods for producing a canola plant by crossing a first parent canola plant with a second parent canola plant wherein the first or second parent canola plant is a canola plant of the variety NQC02CNX21. Further, both first and second parent canola plants can come from the canola variety NQC02CNX21. Thus, any such methods using the canola variety NQC02CNX21 are part of this invention: selfing, backcrosses, hybrid production, crosses to populations, and the like. All plants produced using canola variety NQC02CNX21 as a parent are within the scope of this invention, including those developed from varieties derived from canola variety NQC02CNX21. Advantageously, the canola variety could be used in crosses with other, different, canola plants to produce first generation ($F_1$) canola hybrid seeds and plants with superior characteristics. The variety of the invention can also be used for transformation where exogenous genes are introduced and expressed by the variety of the invention. Genetic variants created either through traditional breeding methods using variety NQC02CNX21 or through transformation of NQC02CNX21 by any of a number of protocols known to those of skill in the art are intended to be within the scope of this invention.

The following describes breeding methods that may be used with canola cultivar NQC02CNX21 in the development of further canola plants. One such embodiment is a method for developing a cultivar NQC02CNX21 progeny canola plant in a canola plant breeding program comprising: obtaining the canola plant, or a part thereof, of cultivar NQC02CNX21 utilizing said plant or plant part as a source of breeding material and selecting a canola cultivar NQC02CNX21 progeny plant with molecular markers in common with cultivar NQC02CNX21 and/or with morphological and/or physiological characteristics selected from the characteristics listed in Tables 1 or 2. Breeding steps that may be used in the canola plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of canola cultivar NQC02CNX21 progeny canola plants, comprising crossing cultivar NQC02CNX21 with another canola plant, thereby producing a population of canola plants, which, on average, derive 50% of their alleles from canola cultivar NQC02CNX21. A plant of this population may be selected and repeatedly selfed or sibbed with a canola cultivar resulting from these successive filial generations. One embodiment of this invention is the canola cultivar produced by this method and that has obtained at least 50% of its alleles from canola cultivar NQC02CNX21.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the invention includes canola cultivar NQC02CNX21 progeny canola plants comprising a combination of at least two cultivar NQC02CNX21 traits selected from the group consisting of those listed in Tables 1 and 2 or the cultivar NQC02CNX21 combination of traits listed in the Summary of the Invention, so that said progeny canola plant is not significantly different for said traits than canola cultivar NQC02CNX21 as determined at the 5% significance level when grown in the same environmental conditions. Using techniques described herein, molecular markers may be used to identify said progeny plant as a canola cultivar NQC02CNX21 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of canola cultivar NQC02CNX21 may also be characterized through their filial relationship with canola cultivar NQC02CNX21, as for example, being within a certain number of breeding crosses of canola cultivar NQC02CNX21. A breeding cross is a cross made to introduce new genetics into the progeny, and is distinguished from a cross, such as a self or a sib cross, made to select among existing genetic alleles. The lower the number of breeding crosses in the pedigree, the closer the relationship between canola cultivar NQC02CNX21 and its progeny. For example, progeny produced by the methods described herein may be within 1, 2, 3, 4 or 5 breeding crosses of canola cultivar NQC02CNX21.

DEPOSIT INFORMATION

A deposit of the Dow AgroSciences LLC canola cultivar NQC02CNX21 disclosed above and recited in the appended claims has been made with the American Type Culture Collection (ATCC), 10801 University Boulevard, Manassas, Va. 20110. The date of deposit was Mar. 25, 2005. The deposit of 2,500 seeds was taken from the same deposit maintained by Dow AgroSciences Plant Genetics and Biotech. since prior to the filing date of this application. All restrictions upon the deposit have been removed, and the deposit is intended to meet all of the requirements of 37 C.F.R. §1.801-1.809. The ATCC accession number is PTA-6644. The deposit will be maintained in the depository for a period of 30 years, or 5 years after the last request, or for the effective life of the patent, whichever is longer, and will be replaced as necessary during that period.

A deposit of the Dow AgroSciences proprietary canola cultivar NQC02CNX12 disclosed above and recited in the appended claims has been made with the American Type Culture Collection (ATCC), 10801 University Boulevard, Manassas, Va. 20110. The date of deposit was May 26, 2004. The deposit of 2,500 seeds were taken from the same deposit maintained by Agrigenetics, Inc. d/b/a Mycogen Seeds since prior to the filing date of this application. All restrictions upon the deposit have been removed, and the deposit is intended to meet all of the requirements of 37 C.F.R. §1.801-1.809. The ATCC accession number is PTA-6011. The deposit will be maintained in the depository for a period of 30 years, or 5 years after the last request, or for the effective life of the patent, whichever is longer, and will be replaced as necessary during that period.

A deposit of the Dow AgroSciences proprietary canola cultivar NQC02CNX25 disclosed above and recited in the appended claims has been made with the American Type Culture Collection (ATCC), 10801 University Boulevard, Manassas, Va. 20110. The date of deposit was May 26, 2004. The deposit of 2,500 seeds were taken from the same deposit maintained by Agrigenetics, Inc. d/b/a Mycogen Seeds since prior to the filing date of this application. All restrictions upon the deposit have been removed, and the deposit is intended to meet all of the requirements of 37 C.F.R. §1.801-1.809. The ATCC accession number is PTA-6012. The deposit will be maintained in the depository for a period of 30 years, or 5 years after the last request, or for the effective life of the patent, whichever is longer, and will be replaced as necessary during that period.

A deposit of the Dow AgroSciences LLC canola cultivar NQC02CNX13 disclosed above and recited in the appended claims has been made with the American Type Culture Collection (ATCC), 10801 University Boulevard, Manassas, Va. 20110. The date of deposit was Mar. 25, 2005. The deposit of 2,500 seeds was taken from the same deposit maintained by Dow AgroSciences Plant Genetics and Biotech. since prior to the filing date of this application. All restrictions upon the deposit have been removed, and the deposit is intended to meet all of the requirements of 37 C.F.R. §1.801-1.809. The ATCC accession number is PTA-6643. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A canola seed comprising imidazolinone resistance, and further comprising oleic acid content in the total seed oil of greater than 70.0% by weight, wherein the seed is obtained from a canola cultivar that is a progeny of crossing canola cultivars 45A71, Nex 705 (ATCC Deposit No. PTA-2087), and Nex 715.

2. The canola seed of claim 1, wherein the oleic acid content is between 70.1% and 72.0% by weight.

3. The canola seed of claim 1, wherein the oleic acid content is between 72.1% and 74.0% by weight.

4. The canola seed of claim 1, wherein the oleic acid content is between 74.1% and 76.0% by weight.

5. The canola seed of claim 1, further comprising less than 3.0% by weight linolenic acid in the total seed oil.

6. The canola seed of claim 5, wherein the linolenic acid content is between 2.0% and 2.99% by weight.

7. The canola seed of claim 5, wherein the linolenic acid content is between 1.0% and 1.99% by weight.

8. The canola seed of claim 5, wherein the linolenic acid content is between 0.5% and 0.99% by weight.

9. A canola plant produced from the seed of claim 1, further comprising blackleg (*Leptosphaeria maculans*) resistance.

10. A canola plant produced from the seed of claim 5, further comprising blackleg (*Leptosphaeria maculans*) resistance.

11. The canola seed of claim 1, further comprising total glucosinolate content of less than 12.0 µm/g of seed.

12. The canola seed of claim 11, the seed comprising total glucosinolate content of between 10.0 µm/g and 11.99 µm/g of seed.

13. The canola seed of claim 11, the seed comprising total glucosinolate content of between 8.0 µm/g and 9.99 µm/g of seed.

14. The canola seed of claim 11, the seed comprising total glucosinolate content of between 7.0 µm/g and 7.99 µm/g of seed.

15. A canola plant produced from the seed of claim 1.

16. The canola seed of claim 1, wherein the seed is obtained from a hybrid canola cultivar obtained by a method comprising:
    crossing canola cultivar 45A71 with canola cultivar Nex 705 (ATCC Deposit No. PTA-2087) to produce an $F_1$ plant;
    backcrossing the $F_1$ plant with canola cultivar Nex 705 to obtain an $F_2$ plant; and
    crossing the $F_2$ plant with canola cultivar Nex 715, thereby producing the hybrid canola cultivar.

17. The canola seed of claim 16, wherein the seed is obtained from the canola cultivar designated NQC02CNX13 (ATCC Deposit No. PTA-6643).

18. A canola plant produced from the seed of claim 16.

19. A canola plant produced from the seed of claim 17.

20. The canola seed of claim 1, wherein the seed is obtained from a single gene conversion of a canola cultivar selected from the group consisting of the cultivar designated NQC02CNX12 (ATCC Deposit No. PTA-6011), the cultivar designated NQC02CNX13 (ATCC Deposit No. PTA-6643), the cultivar designated NQC02CNX25 (ATCC Deposit No. PTA-6012), and the cultivar designated NQC02CNX21 (ATCC Deposit No. PTA-6644).

21. A method of controlling at least one weed in a field, wherein the field contains at least one canola plant of claim 15, the method comprising applying an imidazolinone herbicide to at least a portion of the field that contains the canola plant.

22. The method according to claim 21, wherein the canola plant further comprises glyphosate resistance, the method further comprising applying a glyphosate herbicide to at least a portion of the field.

23. The method according to claim 21, wherein the canola plant further comprises glufosinate resistance, the method further comprising applying a glufosinate herbicide to at least a portion of the field.

24. The method according to claim 21, wherein the canola plant further comprises 2,4-D resistance, the method further comprising applying a 2,4-D herbicide to at least a portion of the field.

* * * * *